United States Patent [19]

Parenti et al.

[11] Patent Number: 5,141,953
[45] Date of Patent: Aug. 25, 1992

[54] PURPUROMYCIN FOR THE TREATMENT OF VAGINAL INFECTIONS AND PHARMACEUTICAL DOSAGE FORMS FOR SAID USE

[75] Inventors: Francesco Parenti, Lainate; Beth P. Goldstein, Milan; Luigi Simioni, Cusano Milanino, all of Italy

[73] Assignee: Gruppo Lepetit S.p.A., Milan, Italy

[21] Appl. No.: 497,378

[22] Filed: Mar. 22, 1990

[30] Foreign Application Priority Data

Mar. 31, 1989 [EP] European Pat. Off. ........ 89105686.3
May 23, 1989 [EP] European Pat. Off. ........ 89109272.8

[51] Int. Cl.$^5$ .............................................. A61K 31/35
[52] U.S. Cl. .................... 514/455; 549/256
[58] Field of Search ................... 514/455; 549/264

[56] References Cited

U.S. PATENT DOCUMENTS 3,914,257  10/1975  Pagani et al. ................ 260/343.2 R

OTHER PUBLICATIONS

Merck Index 10th ed. #7848.
Rambelli et al. CA 110: 168352e 1989.
Coronelli et al. CA 81: 2360p 1974.

Primary Examiner—Frederick E. Waddell
Assistant Examiner—Russell Travers
Attorney, Agent, or Firm—J. Michael Dixon

[57] ABSTRACT

Use of the antibiotic purpuromycin for the topical treatment of infectious vaginitis and topical dosage forms containing said product. The antibiotic purpuromycin is simultaneously active against the main causative agents of infectious vaginitis i.e.: *Candida vaginalis*, *Trichomonas vaginalis* and *Gardnerella vaginalis*.

2 Claims, No Drawings

PURPUROMYCIN FOR THE TREATMENT OF VAGINAL INFECTIONS AND PHARMACEUTICAL DOSAGE FORMS FOR SAID USE

This invention concerns the use of the antibiotic purpuromycin for the topical treatment of infectious vaginitis. The term treatment includes both the cure and the prevention of the infection and re-infection. More particularly, the invention regards the use of purpuromycin for preparing topical dosage forms for combatting and preventing infectious vaginitis and a method of treatment of infectious vaginitis by topically administering purpuromycin to patients affected or exposed to the risk of being affected by the infection or being carriers of the causative agents of the infection.

The term "patient" used herein is taken to mean mammals such as primates (including humans, sheep, horses, cattle, dogs, cats, rats, mice) and birds.

Infectious vaginitis is mainly due to the unbalanced presence in the vagina of fungi, protozoa and bacteria. Several authors have extensively discussed the problem in the medical literature and a complete review on the pathogenesis and treatment of said infections was published by L. V. H. Hill and J. A. Embil in Can. Med. Assoc. J. Vol. 134, pag. 321-331 (1986). Fungal vaginitis is essentially due to the yeast *Candida albicans*. Synthetic imidazoles (e.g. miconozole, econozole, clotrimazole, ketoconozole) and triazoles (e.g. fluconazole), gentian violet, candicidin, amphotericin and nystatin have been described as effective against *Candida albicans* infections. Topically administered nystatin is considered to be the most useful drug for combatting or preventing yeast vaginitis.

Protozoal infections are essentially due to *Trichomonas vaginalis*. Nitroimidazoles (e.g. metronidazole and tinidazole) are active against *Trichomonas vaginalis*. Orally administered metronidazole is recommended for the treatment of said infection although with some important drawbacks due to potential mutagenic and carcinogenic effects which limit its application in pregnant patients (see: D. A. Eschenbach, Clin. Obstet. Gynecol., 26(1), 186-202, 1983).

Vaginitis caused by neither Trichomonas nor yeasts is generally defined as nonspecific vaginitis or bacterial vaginitis and is generally due to bacteria, in particular *Gardnerella vaginalis*. Anaerobic bacteria (*Bacteroides spp., Peptococcus spp., comma-shaped bacteria*) are also frequently present in nonspecific vaginitis (A. Skarin et al. Scand. J. Infect. Dis. Suppl. 40, 81-84, 1983; E. E. Petersen et. al., Scand.J. Suppl 40, 97-99, 1983). Although several Infect. Dis. Suppl. 40, 97-99, 1983). Although several antibiotics and synthetic antibacterials are active against *Gardnerella vaginalis* and the other above mentioned bacteria, administration of metronidazole is the most commonly recommended form of therapy for nonspecific vaginitis.

Simultaneous presence of Gardnerella and other anaerobes in trichomonal infections has often been demonstrated (C. A. Easmon et. al.: J. Clin. Pathol. Vol. 36, 1367-1370, 1983). Metronidazole is active against both *Trichomonas* and *Gardnerella vaginalis*, this justifies the wide use of metronidazole in the therapy of both trichomoniasis and nonspecific vaginitis. However, metronidazole is not active against yeasts and development of yeast vaginitis has been observed under metronidazole treatment (see: F. Fleury, Chemotherapy 28 (suppl. 1), 48-50, 1982). Moreover, strains of *Gardnerella vaginalis* resistant to metronidazole have been isolated (see Table II hereinbelow). To the best knowledge of the inventors, the substances which have been indicated as suitable for the therapy or prevention of each of the three types of infectious vaginitis are not simultaneously effective against *Trichomonas, Candida* and *Gardnerella*.

According to the invention, it has now been found that purpuromycin is active against all three above mentioned pathogenic microorganisms and therefore it may be advantageously employed in the treatment of infectious vaginitis. Accordingly, the main object of this invention is the use of purpuromycin in a method and topical dosage forms for the topical treatment of vaginal infections.

In view of the simultaneous activity against *Candida vaginalis, Trichomonas vaginalis* and *Gardnerella vaginalis*, the use, method and topical dosage forms of this invention are particularly useful for the treatment of patients affected by infectious vaginitis when the causative agents of said infection is not or cannot be unequivocally determined or there is evidence or likelihood of the contemporaneous presence of at least two of the above mentioned pathogenic organisms.

Although good medical practice would prescribe that the diagnosis of infectious vaginitis be supported by etiological determinations, common medical practice, economic, logistic and environmental factors lead to a practical situation in which most of the diagnosis of infectious vaginitis are based only on the symptomatology of the patient. Examination of vaginal smears and microbiological tests are usually carried out only in those cases where the intervention of a specialist is involved because of inefficiency of therapy or recurrence of the infection. Therefore, a medicament which is simultaneously active against all three main causative agents of infectious vaginitis represents valuable progress in the treatment of such disease.

Purpuromycin is an antibiotic produced by *Actinoplanes ianthinogenes nov. sp.* A/1668 which was originally deposited at the Americal Type Culture Collection (ATCC) of Rockville, MD 20852 USA on Jan. 29, 1973 with the number 21884. This strain was accepted under the conditions prescribed by the Budapest Treaty as of Jan. 31, 1981.

Purpuromycin which, according to this invention is useful in the treatment of infectious vaginitis and for the preparation of topical dosage forms for said treatment, is represented by the following general formula:

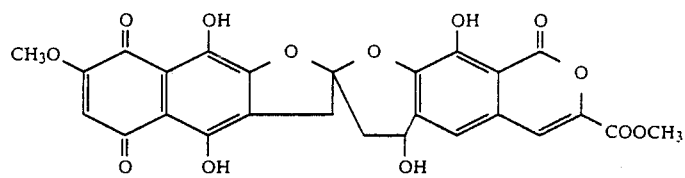

Its preparation is described in UK Patent 1 455 128 wherein is also reported its antimicrobial activity. Accordingly, purpuromycin is shown to be active in vitro against both Gram-positive and Gram-negative bacteria and fungi, including filamentous fungi (e.g., *Trichophyton mentagrophytes*) and yeasts e.g., *Candida albicans*). In the prior art, no indication is given about the activity of purpuromycin against *Trichomonas vaginalis* or against *Gardnerella vaginalis* and other anaerobic bacteria which are known to be, besides *Candida albicans*, the main causative agents of infectious vaginitis.

Representative tests of the activity of purpuromycin against *Trichomonas vaginalis* have been carried out by the two-fold tube dilution method. *Trichomonas vaginalis* (applicant's internal code TVL) was grown on Trichomonas Culture Medium Base (Merck) plus 10% horse serum. Inoculum: approximately $10^5$ organisms/ml. Incubation: 48 hours at 37° C. Purpuromycin was dissolved in dimethylsulfoxide (DMSO) at a concentration of 5 mg/ml and added to the culture medium at the maximum concentration of 128 microgram/ml. Under these conditions purpuromycin showed a minimal inhibitory concentration (M.I.C.) value against Trichomonas vaginalis strain TVL (applicant's internal code) of 4 micrograms/ml.

Comparative experiments with other known antifungal agents showed that usually their activity against *Trichomonas vaginalis* strain TVL is very low or negligible as indicated in the following TABLE I.

TABLE I

Activity of various antifungal agents and metronidazole against *Trichomonas vaginalis* strain TVL

| COMPOUND | MIC (mcg/ml) |
| --- | --- |
| Amphotericin B | 64 |
| Nystatin | >128 |
| Miconazole | 32 |
| Clotrimazole | 64 |
| Ketoconazole | >128 |
| Metronidazole (positive control) | 0.25 |

The activity of purpuromycin and other known antimicrobial agents against *Gardnerella vaginalis* ATCC 14018 and other 11 clinical isolates (identified with applicant's internal codes: L 531, L 1622, L 1623, L 1624, L 1625, L 1626, L 1627, L 1628, L 1629, L 1630, L 1631) has also been determined by standard two-fold dilution methods. The strains were grown on Casman medium (Difco) plus 5% (v/v) whole rabbit blood and 0.15 (v/v) lysed rabbit blood. Inoculum size: approximately $10^4$ colony forming units per spot. Incubation in an anaerobic hood: 48 hours at 37° C.

The data reported in TABLE II show that purpuromycin inhibits the growth of all tested strains at a concentration of 8 micrograms/ml, while the other agents in most cases have lower or negligible activity. It is noteworthy that purpuromycin is active also on strains resistant to metronidazole (MIC >32 micrograms/ml), nystatin (MIC >128 micrograms/ml) and miconozole (MIC 128 micrograms/ml).

TABLE II

Activity of purpuromycin and other antifungal and antiprotozoal agents against *Gardnerella vaginalis*

| COMPOUND | NUMBER OF STRAINS WITH MIC OF: | | | | | | |
| --- | --- | --- | --- | --- | --- | --- | --- |
|  | 4 | 8 | 16 | 32 | 64 | 128 | >128 (mcg/ml) |
| Purpuromycin |  | 12 |  |  |  |  |  |
| Metronidazole | 1 | 3 | 4 |  | 1 | 3 |  |
| Nystatin |  |  |  |  |  |  | 12 |

TABLE II-continued

Activity of purpuromycin and other antifungal and antiprotozoal agents against *Gardnerella vaginalis*

| COMPOUND | NUMBER OF STRAINS WITH MIC OF: | | | | | | |
| --- | --- | --- | --- | --- | --- | --- | --- |
|  | 4 | 8 | 16 | 32 | 64 | 128 | >128 (mcg/ml) |
| Clotrimazole |  | 2 | 1 | 2 | 5 |  | 2 |
| Miconazole | 1 | 7 |  | 2 |  |  | 2 |

The activity of purpuromycin against yeasts was confirmed through experiments carried out with *Candida albicans* ATCC 10231, *Candida albicans* SKF 2270 and 19 clinical isolates (applicant's internal code L 1404, L 1405, L 1406, L 1407, L 1408, L 1409, L 1410, L 1411, L 1412, L 1413, L 1414, L 1415, L 1416, L 1417, L 1418, L 1429, L 1430, L 1431, L 1432).

This set of experiments included also one strain each of two other Candida species, *Candida tropicalis* and *Candida kruzei*. The M.I.C. were determined by the two-fold dilution method in buffered (0.01 M phosphate buffer, pH 7.4) yeast nitrogen base medium (Difco) supplemented with 1.5 g/liter asparagine in microliter plates. Inocula were approximately $10^4$ colony forming units/ml. Incubation was for 20 h at 30° C. Purpuromycin was dissolved in DMSO and added to the cultures as above. The following TABLE III reports the MIC values for the whole set of strains.

TABLE III

Activity of purpuromycin against Candida strains

| Species (number of strains) | MIC (micrograms/ml) |
| --- | --- |
| *Candida albicans* (19 clinical isolates, MIC range) | 1–4 |
| *Candida albicans* SKF 2270 | 1 |
| *Candida albicans* ATCC 10231 | 0.5 |
| *Candida tropicalis* L 243 | 2 |
| *Candida kruzei* L 244 | 4 |

In comparative tests a series of antibacterial agents (penicillin G, ampicillin, cefalexin, cefoxitin, cephaloridine, clindamycin, erythromycin, chloramphenicol, tetracycline, gentamicin, spectinomycin, metronidazole, sulfamethoxazole) which are known to be active against *Gardnerella vaginalis* (see: S. Shanker et. al.: Eur. J. Clin. Microbiol., October 1982, 298–300) showed in all cases M.I.C. values higher than 128 microgram/ml. against both *Candida albicans* SKF 2270 and *Candida albicans* ATCC 10231.

The effectiveness of purpuromycin in the topical treatment of yeast vaginal infection was also tested in ovariectomized rats (Charles River) treated subcutaneously with 4 mg of estradiol benzoate approximately two weeks after ovariectomy. Five days later they were inoculated intravaginally with approximately $5 \times 10^6$ colony forming units (CFU) of *Candida albicans* strain SKF 2270 in 25 microliters of Nutrient Broth (no.2, Oxoid) containing 15% (vol/vol) of glycerol. Topical intravaginal therapy was twice daily for three days, starting one day after infection, with 100 microliters of a purpuromycin suspension in a mixture of 10:90 DMSO-polyethylene glycol 400, corresponding to 2 or 5 mg/rat/treatment. The day after the last treatment, vaginal smear samples (calibrated 10 microliter loops) were diluted and plated for viable organism counts on Sabouraud agar (Difco). Each group contained 10 animals. As can be seen from the Table IV, animals treated with purpuromycin had significantly reduced numbers of viable yeast cells/sample.

TABLE IV

Topical antifungal activity of purpuromycin in rats

| Group | Treatment | Mean $\log_{10}$CFU/smear sample ± SD |
|---|---|---|
| 1 | none | 3.43 ± 0.55 |
| 2 | vehicle | 3.74 ± 0.60 |
| 3 | Purpuromycin (2 mg) | 2.00 ± 0.75 |
| 4 | Purpuromycin (5 mg) | 2.28 ± 0.78* |

*P <0.01 vs group 1 controls
CFU = colony forming unit
SD = standard deviation

A further experiment representative of the activity of purpuromycin against other anaerobic bacteria which are usually associated with infectious vaginitis utilized *Bacteroides fragilis* ATCC 25745 as the test microorganism. The experiment was carried out by the two-fold dilution method in microliter plates using Wilkins-Chalgren broth (Difco).

Inoculum size: approximately $10^4$ colony forming units/ml. Incubation in an anerobic hood: 48 hours at 37° C. Purpuromycin was dissolved in DMSO and was added to the culture medium as above. Under the above conditions purpuromycin showed a MIC value of 0.25 microgram/ml against *Bacteroides fragilis* ATCC 23745.

The above findings make purpuromycin particularly suitable for the treatment of vaginal infections. Accordingly, one of the objects of this invention is to provide a method for combatting and/or preventing vaginal infections caused by fungi, protozoa, and bacteria, in particular, *Candida albicans*, *Trichomonas vaginalis* and *Gardnerella vaginalis*, which comprises topically administering to the patient in need thereof an amount of purpuromycin capable of inhibiting the growth of the above mentioned microorganisms.

According to the most recent views of the chemotherapy of vaginal infections, the patients in need of said treatment may be both the female affected by the infection and, in the case of chronic recurrent infections, also her male sexual partner. A further object of this invention is to provide pharmaceutical dosage forms particularly useful for the topical administration of purpuromycin in the treatment of vaginal infections. As purpuromycin is a solid practically unsoluble in water and in lower alkanols, the preparation of topical dosage forms suitable for the treatment of infectious vaginitis is a problem requiring specific solutions. According to this invention topical dosage forms are provided including vaginal tablets, pessaries, creams, ointments, gels, suppositories, lotions, foams, powder, suspensions, drug delivery systems and the like which permit delivery and release of the active substance into the infection sites.

The pharmaceutical dosage forms contain purpuromycin and one or more excipients such as for example: starch, lactose, glucose, talc, cellulose for solid dosage forms; methocel, modified vegetable oils, mineral oils, polyalkylene glycols, fatty acids and alcohols and the like for semi-solid dosage forms; water, alkanols, glycerol, lanolin, polyethylene glycols, mineral oil, pharmaceutically acceptable organic solvents (e.g. DMSO, methyl-decyl-sulfoxide) and the like for liquid or semi-liquid dosage forms. The dosage forms may optionally contain other active ingredients or ingredients which preserve and favor the antimicrobial action of purpuromycin in the infection sites (e.g. antiseptics, emulsifiers, surfactants and the like).

Useful indications for the preparations of suitable topical dosage forms can be found in: Remington's Pharmaceutical Sciences, 17th Edition, 1985 (Mack Publishing Company, Easton, PA)

According to a preferred embodiment of this invention purpuromycin is employed in a micronized or ultramicronized form. Typical micronized and ultramicronized forms of purpuromycin for use in the manufacture of pharmacological dosage forms of this invention have a particle size, for at least 85 per cent of their total weight, of less than 10 and 5 micron diameter, respectively.

The micronization may be carried out using different machinery based on different principles, as known to the person skilled in the art. According to a preferred embodiment of the invention, said micronization is carried out by a fluid energy mill as such or mixed with the appropriate excipients. With this system, the compound to be micronized is propelled by a violent gas stream into a circuit. Collisions of the compound particles against the walls of the circuit, as well as collisions of the particles with each other, lead to the pulverization of the particles. This machine can also be equipped with a recycling device that carries the larger, insufficiently pulverized particles, back into the grinding chamber. The major advantage of the fluid-energy mill lies in the fact that the build-up of the temperature in the micronization chamber is very low and the powder thus obtained is very homogeneous in particle-size, i.e. the range of particle-sizes is vary narrow.

The particle-size of the product may be measured with the HIAC system. In this system the particle-size determination is based on the shadow caused by a particle hit by a light beam. The instrument essentially consists of a sensor which is formed by a light source and a photodetector on either side of the counting cell. A suspension of the test powder in water passes through this cell, the dimensions of which vary depending on the size range to be measured. Each particle, individually, interrupts some portion of a light beam generating a signal which is proportional to the area of the shadow of the particle.

This electric signal, suitably correlated to the diameter of a spherical standard particle which gives the same light absorption, yields the number of particles having a preselected diameter. The instrument may subdivide the measurement range (1-300 micron) in intervals of arbitrarily preset dimensions. By this process it is possible to calculate the number of particles for each measurement range and correlate this number with the total number of particles contained in the sample.

The amount of active substance in the finished dosage forms depends on the minimal inhibitory concentration of purpuromycin against the infection causative agents and its particular type of formulation.

The dosage may obviously be adjusted according to the severity of the infection and the type of patients. Experimental tests for determining the sensitivity of the microorganisms isolated from the patient may also offer useful indication to select the appropriate dosage. In general terms, the effective dosage ranges between 10 and 600 mg, preferably 100 and 400 mg, for each vaginal application once to three times daily. The course of treatment may last from 3 to 10 days or longer, if required.

Liquid or semi-liquid dosage forms such as, creams, lotions, ointments, foams and suspensions generally contains from 0.05 to 5 percent by weight of purpuromycin. If necessary, this range may be broadened without any substantial modification of the characteristics of the respective dosage form. Solid intravaginal unit dosage forms such as vaginal tablets and suppositories can be manufactured in different dosages. For instance, they may contain from 10 to 600 mg of purpuromycin. Preferred dosages are comprised between 100 and 400 mg.

Typical drug delivery systems incorporating purpuromycin are formulated, for instance, with biodegradable polymers for controlled release such as those described at pages 106–119 of the book: Drug Delivery Systems. Fundamentals and Techniques—Edited by P. Johnson and J. G. Loyd-Jones, 1987, Ellis Horwood Ltd. Chichester, England.

EXAMPLES

The following examples show some pharmaceutical dosage forms of purpuromycin for topical treatment of infectious vaginitis. The manufacture of the dosage forms is carried out according to commonly known procedures.

EXAMPLE 1

Vaginal suppositories (hydrophilic)

| | |
|---|---|
| Purpuromycin (micronized) | g 0.30 |
| Methyl-decyl-sulfoxide | g 0.30 |
| Carbowax 4000 | g 1.70 |
| Carbowax 1540 | g 0.80 |
| PEG 1000 monostearate | g 1.30 |

EXAMPLE 2

Vaginal tablets

| | |
|---|---|
| Purpuromycin (micronized) | g 0.300 |
| Lactose | g 0.096 |
| Sodium benzoate | g 0.030 |
| PVP K 30 | g 0.050 |
| Sodium bicarbonate | g 0.134 |
| Sodium citrate, acid | g 0.350 |

EXAMPLE 3

Anhydrous cream

| | |
|---|---|
| Purpuromycin (micronized) | g 2.00 |
| Methyl-decyl-sulfoxide | g 2.00 |
| Carbowax 6000 | g 25.00 |
| Stearyl alcohol | g 10.00 |
| Propylene glycol | g 61.00 |

EXAMPLE 4

Cream (o/w)

| | |
|---|---|
| Purpuromycin (micronized) | g 2.00 |
| White petrolatum | g 12.00 |
| Liquid paraffin | g 12.00 |
| Cetyl alcohol | g 8.50 |
| Stearyl alcohol | g 3.50 |
| Sorbitan monolaurate | g 3.10 |
| Polyoxyethylene sorbitan monolaurate | g 2.30 |
| Methyl-decyl-sulfoxide | g 2.00 |
| Water q.s. to | g 100 |

EXAMPLE 5

Gel

| | |
|---|---|
| Purpuromycin (micronized) | g 2.00 |
| Methyl-decyl-sulfoxide | g 2.00 |
| Propylene glycol | g 8.00 |
| Carbopol 934 | g 2.00 |
| Water q.s. to | g 100 |

EXAMPLE 6

Vaginal foam

| | |
|---|---|
| Purpuromycin (micronized) | g 2.00 |
| Methyl-decyl-sulfoxide | g 2.00 |
| Octyl alcohol | g 0.87 |
| Stearyl alcohol | g 0.35 |
| Polyoxyethylene sorbitan monolaurate | g 0.23 |
| Sorbitan monolaurate | g 0.31 |
| Water | g 83.74 |
| Propellant gas | g 10.50 |

EXAMPLE 7

Soft gelatin capsules

The capsules have an inert covering which dissolves promptly in the vagina. The covering is composed of gelatin, glycerin, water, methylparaben, propyl paraben and coloring. The inside content has the following composition:

| | |
|---|---|
| Purpuromycin (micronized) | g 0.30 |
| Lactose | g 0.10 |
| Polysorbate 80 | g 0.03 |
| Cremophor ® RH 40 | g 0.30 |
| Cremophor ® RH 60 | g 3.47 |

We claim:
1. A method for the treatment of *Trichomonas vaginalis* in a patient comprising topically administering an effective amount of purpuromycin to the patient.
2. A method according to claim 1 in which the patient is intravaginally administered from 10–600 mg of purpuromycin per does, from 1 to 3 times daily.

* * * * *